(12) United States Patent
Duindam et al.

(10) Patent No.: US 11,800,991 B2
(45) Date of Patent: Oct. 31, 2023

(54) GRAPHICAL USER INTERFACE FOR CATHETER POSITIONING AND INSERTION

(71) Applicant: Intuitive Surgical Operations Inc., Sunnyvale, CA (US)

(72) Inventors: Vincent Duindam, San Francisco, CA (US); Carol Reiley, Mountain View, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 1281 days.

(21) Appl. No.: 14/910,601

(22) PCT Filed: Aug. 12, 2014

(86) PCT No.: PCT/US2014/050715
§ 371 (c)(1),
(2) Date: Feb. 5, 2016

(87) PCT Pub. No.: WO2015/023665
PCT Pub. Date: Feb. 19, 2015

(65) Prior Publication Data
US 2016/0183841 A1 Jun. 30, 2016

Related U.S. Application Data

(60) Provisional application No. 61/866,327, filed on Aug. 15, 2013.

(51) Int. Cl.
*A61B 5/06* (2006.01)
*A61M 25/01* (2006.01)
(Continued)

(52) U.S. Cl.
CPC .............. *A61B 5/066* (2013.01); *A61B 5/743* (2013.01); *A61B 17/34* (2013.01); *A61B 34/25* (2016.02);
(Continued)

(58) Field of Classification Search
None
See application file for complete search history.

(56) References Cited

U.S. PATENT DOCUMENTS

| 5,638,819 A | 6/1997 | Manwaring et al. |
| 6,380,732 B1 | 4/2002 | Gilboa |

(Continued)

FOREIGN PATENT DOCUMENTS

| CN | 102395327 A | 3/2012 |
| EP | 1103229 A2 | 5/2001 |

(Continued)

OTHER PUBLICATIONS

Definition of Concentric by Merriam-Webster, pub. online at <https://www.merriam-webster.com/dictionary/concentric>, accessed on Jul. 21, 2019 (Year: 2019).*

(Continued)

*Primary Examiner* — Christopher Koharski
*Assistant Examiner* — Michael S Kellogg
(74) *Attorney, Agent, or Firm* — HAYNES AND BOONE, LLP

(57) ABSTRACT

A method of guiding an interventional instrument within a patient anatomy comprises processing a target location within the patient anatomy and receiving a position for a tip portion of an interventional instrument at a first location within the patient anatomy. The method also comprises determining a three-dimensional distance between the first location and the target location and displaying a symbol (Continued)

representing the target location and a symbol representing the tip portion of the interventional instrument.

20 Claims, 7 Drawing Sheets

(51) Int. Cl.
*A61B 34/00* (2016.01)
*A61B 17/34* (2006.01)
*A61B 5/00* (2006.01)
*A61B 34/10* (2016.01)
*A61B 34/30* (2016.01)
*A61B 34/20* (2016.01)
*A61B 10/04* (2006.01)

(52) U.S. Cl.
CPC ........ *A61M 25/01* (2013.01); *A61M 25/0105* (2013.01); *A61B 34/30* (2016.02); *A61B 2010/045* (2013.01); *A61B 2034/107* (2016.02); *A61B 2034/2051* (2016.02); *A61B 2034/2061* (2016.02); *A61M 2025/0166* (2013.01)

(56) References Cited

U.S. PATENT DOCUMENTS

| | | | |
|---|---|---|---|
| 6,389,187 B1 | 5/2002 | Greenaway et al. | |
| 6,671,538 B1 | 12/2003 | Ehnholm et al. | |
| 7,930,065 B2 | 4/2011 | Larkin et al. | |
| 8,102,416 B2 | 1/2012 | Ito et al. | |
| 8,412,307 B2 | 4/2013 | Willis et al. | |
| 2004/0082849 A1 | 4/2004 | Schweikard et al. | |
| 2006/0013523 A1 | 1/2006 | Childlers et al. | |
| 2006/0189842 A1 | 8/2006 | Hoeg et al. | |
| 2007/0065077 A1 | 3/2007 | Childers et al. | |
| 2007/0270650 A1 | 11/2007 | Eno et al. | |
| 2008/0212082 A1 | 9/2008 | Froggatt et al. | |
| 2010/0076305 A1 | 3/2010 | Maier-Hein et al. | |
| 2010/0179418 A1 | 7/2010 | Mueller et al. | |
| 2010/0217117 A1* | 8/2010 | Glossop | A61B 8/4245 600/424 |
| 2010/0249506 A1 | 9/2010 | Prisco | |
| 2010/0317965 A1 | 12/2010 | Itkowitz et al. | |
| 2012/0065481 A1 | 3/2012 | Hunter et al. | |
| 2012/0289777 A1 | 11/2012 | Chopra et al. | |
| 2013/0204124 A1* | 8/2013 | Duindam | A61B 17/3468 600/424 |

FOREIGN PATENT DOCUMENTS

| | | |
|---|---|---|
| JP | H08332191 A | 12/1996 |
| JP | 2004513684 A | 5/2004 |
| JP | 2011050621 A | 3/2011 |
| JP | 2013513462 A | 4/2013 |
| WO | WO-9729709 A1 | 8/1997 |
| WO | WO-0224051 A2 | 3/2002 |
| WO | WO-2011102012 A1 | 8/2011 |

OTHER PUBLICATIONS

Definition of Concentric by Google, pub. online at <https://www.google.com/search?q=dictionary+concentric&rlz=1C1GCEB_enUS800US801&oq=dictionary+concentric&aqs=chrome.0.69i59j69i60j0l4.911j0j7&sourceid=chrome&ie=UTF-8>, accessed on Jul. 21, 2019 (Year: 2019).*
Extended European Search Report for Application No. EP14836490.4, dated Mar. 24, 2017, 9 pages.
International Search Report and Written Opinion for Application No. PCT/US2014/050715, dated Nov. 13, 2014, 17 pages.
International Preliminary Report on Patentability for Application No. PCT/US2014/050715, dated Feb. 25, 2016, 14 pages.
Verut, Jean and Phillipe Coiffet, Robot Technology; Teleoperation and Robotics Evolution and Development, English translation, Prentice-Hall, Inc., Inglewood Cliffs, NJ, USA 1986, vol. 3A, 332 pages.

* cited by examiner

GRAPHICAL USER INTERFACE FOR CATHETER POSITIONING AND INSERTION

CROSS-REFERENCE TO RELATED APPLICATIONS

This application claims the benefit of International Patent Application PCT/US2014/050715 (filed Aug. 12, 2014); which claims priority from U.S. Provisional Application 61/866,327 filed Aug. 15, 2013, which are incorporated by reference herein in their entireties.

FIELD

The present disclosure is directed to systems and methods for navigating a patient anatomy to conduct a minimally invasive procedure, and more particularly to apparatus and methods for using a graphical user interface to assist interventional instrument guidance.

BACKGROUND

Minimally invasive medical techniques are intended to reduce the amount of tissue that is damaged during interventional procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert interventional instruments (including surgical, diagnostic, therapeutic, or biopsy instruments) to reach a target tissue location. To reach the target tissue location, a minimally invasive interventional instrument may navigate natural or surgically created passageways in anatomical systems such as the lungs, the colon, the intestines, the kidneys, the heart, the circulatory system, or the like. Teleoperated interventional systems may be used to insert and position the interventional instrument within the patient anatomy. Position guidance systems are needed to assist clinicians in guiding the interventional instrument to a location in the patient anatomy from which the interventional procedure will be conducted.

SUMMARY

The embodiments of the invention are summarized by the claims that follow the description.

In one embodiment, a method of guiding an interventional instrument within a patient anatomy comprises processing a target location within the patient anatomy and receiving a position for a tip portion of an interventional instrument at a first location within the patient anatomy. The method also comprises determining a three-dimensional distance between the first location and the target location and displaying a symbol representing the target location and a symbol representing the tip portion of the interventional instrument.

In another embodiment, a system comprises non-transitory computer readable media containing computer executable instructions for guiding an interventional instrument within a patient anatomy including instructions for processing a target location within the patient anatomy. The non-transitory computer readable media further containing computer executable instructions for receiving a position of a tip portion of an interventional instrument at a first location within the patient anatomy, determining a three-dimensional distance between the first location and the target location, and displaying a symbol representing the target location and a symbol representing the tip portion of the interventional instrument.

In another embodiment, a method of guiding an interventional instrument within a patient anatomy comprises processing a target location within the patient anatomy and receiving a first position indication for a tip portion of an interventional instrument at a first location within the patient anatomy. The method further comprises concurrently displaying a navigation aid image, including a symbol representing the target location, a symbol representing the tip portion of the interventional instrument, a symbol representing a direction between the first position and the target location, and a symbol representing an insertion distance component between the first position and the target location in a first window, with an endoscopic camera image in a second window, a virtual endoscopic modeled image in a third window, a virtual pathway modeled image in a fourth window, and a pre-operative image of the patient anatomy with a mark at the target location in a fifth window.

Additional aspects, features, and advantages of the present disclosure will become apparent from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an elongated object.

Figure 1:
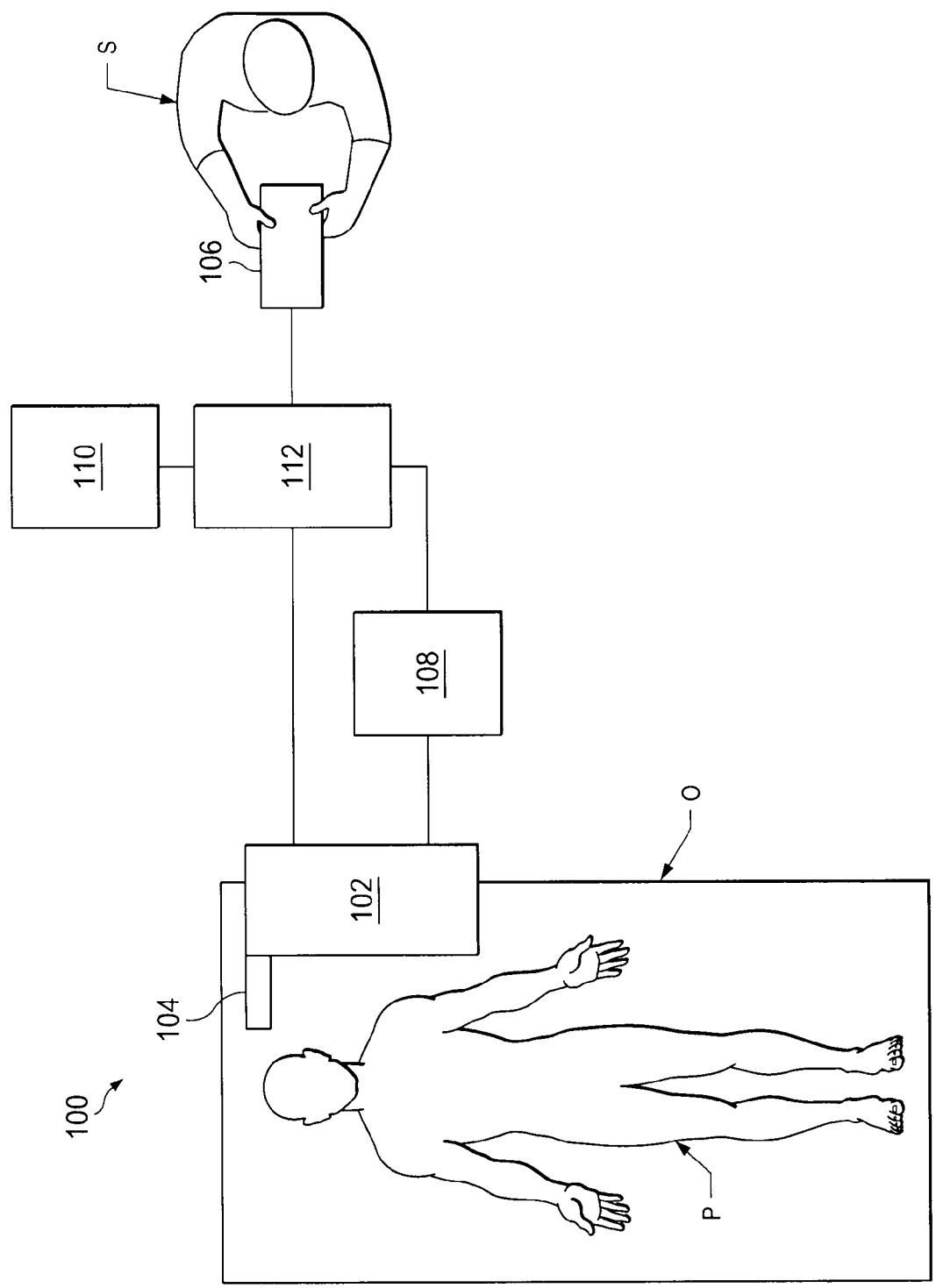
FIG. 1 is a robotic interventional system, in accordance with an embodiment of the present disclosure.

Referring to FIG. 1 of the drawings, a robotic interventional system for use in, for example, surgical, diagnostic, therapeutic, or biopsy procedures, is generally indicated by the reference numeral 100. As will be described, the robotic interventional systems of this disclosure are generally under the teleoperational control of a surgeon. However, for some procedures or sub-procedures, the robotic interventional system may be under the partial or full control of a computer programmed to perform the procedure or sub-procedure. As shown in FIG. 1, the robotic interventional system 100 generally includes a robotic assembly 102 mounted to or near an operating table O on which a patient P is positioned. An interventional instrument system 104 is operably coupled to the robotic assembly 102. An operator input system 106 allows a surgeon or other type of clinician S to view the surgical site and to control the operation of the interventional instrument system 104.

The operator input system 106 may be located at a surgeon's console which is usually located in the same room as operating table O. However, it should be understood that the surgeon S can be located in a different room or a completely different building from the patient P. Operator input system 106 generally includes one or more control device(s) for controlling the interventional instrument system 104. The control device(s) may include any number of a variety of input devices, such as hand grips, joysticks, trackballs, data gloves, trigger-guns, hand-operated controllers, voice recognition devices, touch screens, body motion or presence sensors, or the like. In some embodiments, the control device(s) will be provided with the same degrees of freedom as the interventional instruments of the robotic assembly to provide the surgeon with telepresence, or the perception that the control device(s) are integral with the instruments so that the surgeon has a strong sense of directly controlling instruments. In other embodiments, the control device(s) may have more or fewer degrees of freedom than the associated interventional instruments and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, or the like).

The robotic assembly 102 supports the interventional instrument system 104 and may comprise a kinematic structure of one or more non-servo controlled links (e.g., one or more links that may be manually positioned and locked in place, generally referred to as a set-up structure) and a robotic manipulator. The robotic assembly 102 includes plurality of actuators (e.g., motors) that drive inputs on the interventional instrument 104. These motors actively move in response to commands from the control system (e.g., control system 112). The motors include drive systems which when coupled to the interventional instrument 104 may advance the interventional instrument into a naturally or surgically created anatomical orifice and/or may move the distal end of the interventional instrument in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, the motors can be used to actuate an articulable end effector of the instrument for grasping tissue in the jaws of a biopsy device or the like.

The robotic interventional system 100 also includes a sensor system 108 with one or more sub-systems for receiving information about the instruments of the robotic assembly. Such sub-systems may include a position sensor system (e.g., an electromagnetic (EM) sensor system); a shape sensor system for determining the position, orientation, speed, pose, and/or shape of the catheter tip and/or of one or more segments along a flexible body of instrument 104; and/or a visualization system for capturing images from the distal end of the catheter system.

The robotic interventional system 100 also includes a display system 110 for displaying an image of the surgical site and interventional instruments 104 generated by subsystems of the sensor system 108. The display 110 and the operator input system 106 may be oriented so the operator can control the interventional instrument system 104 and the operator input system 106 as if viewing the workspace in substantially true presence. True presence means that the displayed tissue image appears to an operator as if the operator was physically present at the image location and directly viewing the tissue from the perspective of the image.

Alternatively or additionally, display system 110 may present images of the surgical site recorded and/or modeled preoperatively or intra-operatively using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. The presented preoperative or intra-operative images may include two-dimensional, three-dimensional, or four-dimensional (including e.g., time based or velocity based information) images and models.

In some embodiments, the display system 110 may display a virtual visualization image in which the actual location of the interventional instrument is registered (e.g., dynamically referenced) with preoperative or concurrent images to present the surgeon with a virtual image of the internal surgical site at the location of the tip of the surgical instrument.

In other embodiments, the display system 110 may display a virtual visualization image in which the actual location of the interventional instrument is registered with prior images (including preoperatively recorded images) or concurrent images to present the surgeon with a virtual image of an interventional instrument at the surgical site. An image of a portion of the interventional instrument 104 may be superimposed on the virtual image to assist the surgeon controlling the interventional instrument.

The robotic interventional system 100 also includes a control system 112. The control system 112 includes at least one memory and at least one processor (not shown), and typically a plurality of processors, for effecting control between the interventional instrument system 104, the operator input system 106, the sensor system 108, and the display system 110. The control system 112 also includes programmed instructions (e.g., a computer-readable medium storing the instructions) to implement some or all of the methods described herein. While control system 112 is shown as a single block in the simplified schematic of FIG. 1, the system may comprise a number of data processing circuits with a portion of the processing optionally being performed on or adjacent the robotic assembly 102, a portion being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the robotic systems described herein. In one embodiment, control system 112 supports wireless communication protocols such as Bluetooth, IrDA, HomeRF, IEEE 802.11, DECT, and Wireless Telemetry.

In some embodiments, control system 112 may include one or more servo controllers to provide force and torque feedback from the interventional instrument system 104 to one or more corresponding servomotors for the operator input system 106. The servo controller(s) may also transmit signals instructing robotic assembly 102 to move the interventional instruments 104 which extend into an internal surgical site within the patient body via openings in the body. Any suitable conventional or specialized servo controller may be used. A servo controller may be separate from, or integrated with, robotic assembly 102. In some embodiments, the servo controller and robotic assembly are provided as part of a robotic arm cart positioned adjacent to the patient's body.

The control system 112 may further include a virtual visualization system to provide navigation assistance to the interventional instruments 104. Virtual navigation using the virtual visualization system is based upon reference to an acquired dataset associated with the three dimensional structure of the anatomical passageways. More specifically, the virtual visualization system processes images of the surgical site recorded and/or modeled using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software is used to convert the recorded images into a two dimensional or three dimensional model of a partial or an entire anatomical organ or anatomical region. The model describes the various locations and shapes of the passageways and their connectivity. The images used to generate the model may be recorded preoperatively or intra-operatively during a clinical procedure. In an alternative embodiment, a virtual visualization system may use standard models (i.e., not patient specific) or hybrids of a standard model and patient specific data. The model and any virtual images generated by the model may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the patient anatomy. The location can be used to produce both macro-level tracking images of the patient anatomy and virtual internal images of the patient anatomy. Various systems for using fiber optic sensors to register and display an interventional implement together with preoperatively recorded surgical images, such as those from a virtual visualization system, are known. For example U.S. patent application Ser. No. 13/107,562, filed May 13, 2011, disclosing, "Medical System Providing Dynamic Registration of a Model of an Anatomical Structure for Image-Guided Surgery," which is incorporated by reference herein in its entirety, discloses one such system.

The robotic interventional system 100 may further include optional operation and support systems (not shown) such as illumination systems, steering control systems, irrigation systems, and/or suction systems. In alternative embodiments, the robotic system may include more than one robotic assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 2:
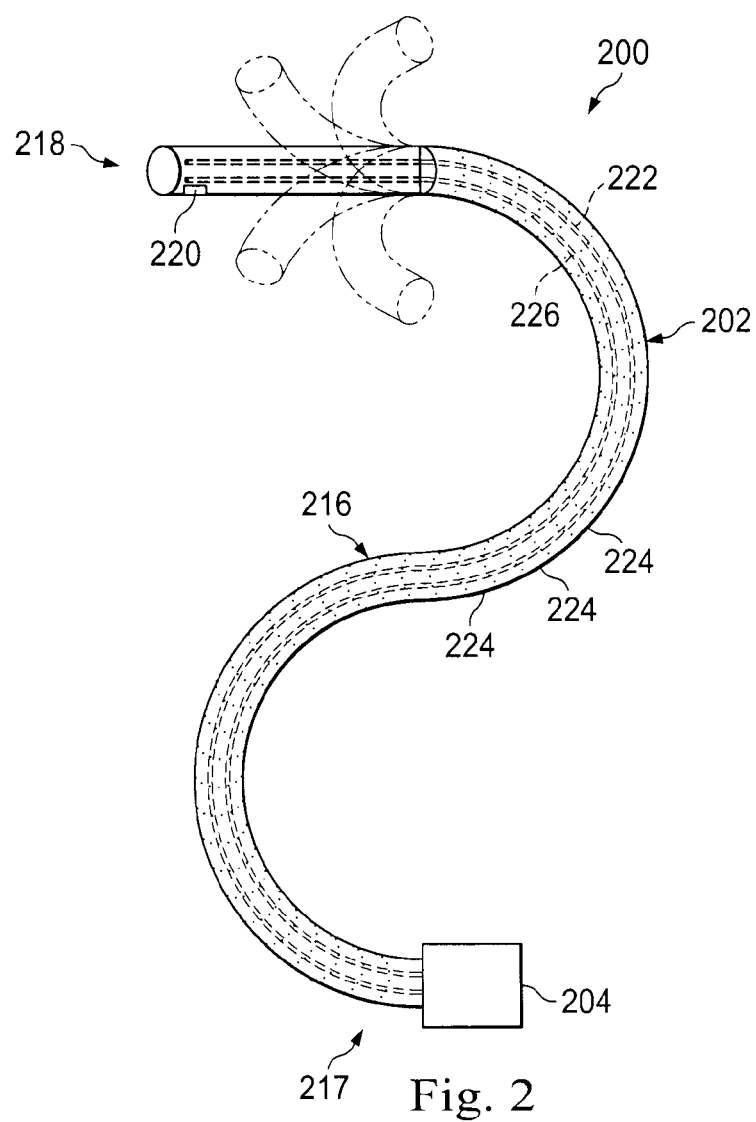
FIG. 2 illustrates an interventional instrument system utilizing aspects of the present disclosure.

FIG. 2 illustrates an interventional instrument system 200 which may be used as the interventional instrument system 104 of robotic interventional system 100. Alternatively, the interventional instrument system 200 may be used for non-robotic exploratory procedures or in procedures involving traditional manually operated interventional instruments, such as endoscopy.

The instrument system 200 includes a catheter system 202 coupled to an instrument body 204. The catheter system 202 includes an elongated flexible catheter body 216 having a proximal end 217 and a distal end or tip portion 218. In one embodiment, the flexible body 216 has an approximately 3 mm outer diameter. Other flexible body outer diameters may be larger or smaller. The catheter system 202 may optionally include a shape sensor 222 for determining the position, orientation, speed, pose, and/or shape of the catheter tip at distal end 218 and/or of one or more segments 224 along the body 216. The entire length of the body 216, between the distal end 218 and the proximal end 217 may be effectively divided into the segments 224. If the instrument system 200 is an interventional instrument system 104 of a robotic interventional system 100, the shape sensor 222 may be a component of the sensor system 108. If the instrument system 200 is manually operated or otherwise used for non-robotic procedures, the shape sensor 222 may be coupled to a tracking system that interrogates the shape sensor and processes the received shape data.

The shape sensor system 222 may include an optical fiber aligned with the flexible catheter body 216 (e.g., provided within an interior channel (not shown) or mounted externally). In one embodiment, the optical fiber has a diameter of approximately 200 μm. In other embodiments, the dimensions may be larger or smaller.

The optical fiber of the shape sensor system 222 forms a fiber optic bend sensor for determining the shape of the catheter system 202. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389, filed Jul. 13, 2005, disclosing "Fiber optic position and shape sensing device and method relating thereto;" U.S. Provisional Pat. App. No. 60/588,336, filed on Jul. 16, 2004, disclosing "Fiber-optic shape and relative position sensing;" and U.S. Pat. No. 6,389,187, filed on Jun. 17, 1998, disclosing "Optical Fibre Bend Sensor," which are incorporated by reference herein in their entireties. In other alternatives, sensors employing other strain sensing techniques such as Rayleigh scattering, Raman scattering, Brillouin scattering, and Fluorescence scattering may be suitable. In other alternative embodiments, the shape of the catheter may be determined using other techniques. For example, if the history of the catheter's distal tip pose is stored for an interval of time, the pose history can be used to reconstruct the shape of the device over the interval of time. As another example, historical pose, position, or orientation data may be stored for a known point of an instrument along a cycle of alternating motion, such as breathing. This stored data may be used to develop shape information about the catheter. Alternatively, a series of positional sensors, such as EM sensors, positioned along the catheter can be used for shape sensing. Alternatively, a history of data from a positional sensor, such as an EM sensor, on the instrument during a procedure may be used to represent the shape of the instrument, particularly if an anatomical passageway is generally static. Alternatively, a wireless device with position or orientation controlled by an external magnetic field may be used for shape sensing. The history of its position may be used to determine a shape for the navigated passageways.

In this embodiment, the optical fiber may include multiple cores within a single cladding. Each core may be single-mode with sufficient distance and cladding separating the cores such that the light in each core does not interact significantly with the light carried in other cores. In other embodiments, the number of cores may vary or each core may be contained in a separate optical fiber.

In some embodiments, an array of FBG's is provided within each core. Each FBG comprises a series of modulations of the core's refractive index so as to generate a spatial periodicity in the refraction index. The spacing may be chosen so that the partial reflections from each index change add coherently for a narrow band of wavelengths, and therefore reflect only this narrow band of wavelengths while passing through a much broader band. During fabrication of the FBG's, the modulations are spaced by a known distance, thereby causing reflection of a known band of wavelengths. However, when a strain is induced on the fiber core, the spacing of the modulations will change, depending on the amount of strain in the core. Alternatively, backscatter or other optical phenomena that vary with bending of the optical fiber can be used to determine strain within each core.

Thus, to measure strain, light is sent down the fiber, and characteristics of the returning light are measured. For example, FBG's produce a reflected wavelength that is a function of the strain on the fiber and its temperature. This FBG technology is commercially available from a variety of sources, such as Smart Fibres Ltd. of Bracknell, England. Use of FBG technology in position sensors for robotic surgery is described in U.S. Pat. No. 7,930,065, filed Jul. 20, 2006, disclosing "Robotic Surgery System Including Position Sensors Using Fiber Bragg Gratings," which is incorporated by reference herein in its entirety.

When applied to a multicore fiber, bending of the optical fiber induces strain on the cores that can be measured by monitoring the wavelength shifts in each core. By having two or more cores disposed off-axis in the fiber, bending of the fiber induces different strains on each of the cores. These strains are a function of the local degree of bending of the fiber. For example, regions of the cores containing FBG's, if located at points where the fiber is bent, can thereby be used to determine the amount of bending at those points. These data, combined with the known spacings of the FBG regions, can be used to reconstruct the shape of the fiber. Such a system has been described by Luna Innovations. Inc. of Blacksburg, Va.

As described, the optical fiber may be used to monitor the shape of at least a portion of the catheter system 202. More specifically, light passing through the optical fiber is processed to detect the shape of the catheter system 202 and for utilizing that information to assist in surgical procedures. The sensor system (e.g. sensor system 108) may include an interrogation system for generating and detecting the light used for determining the shape of the catheter system 202. This information, in turn, can be used to determine other related variables, such as velocity and acceleration of the parts of an interventional instrument. The sensing may be limited only to the degrees of freedom that are actuated by the robotic system, or may be applied to both passive (e.g., unactuated bending of the rigid members between joints) and active (e.g., actuated movement of the instrument) degrees of freedom.

The interventional instrument system may optionally include a position sensor system 220. The position sensor system 220 may be an electromagnetic (EM) sensor system that includes one or more conductive coils that may be subjected to an externally generated electromagnetic field. Each coil of the EM sensor system 220 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of an EM sensor system is provided in U.S. Pat. No. 6,380,732, filed Aug. 11, 1999, disclosing "Six-Degree of Freedom Tracking System Having a Passive Transponder on the Object Being Tracked," which is incorporated by reference herein in its entirety.

The flexible catheter body 216 includes a channel sized and shaped to receive an auxiliary tool 226. Auxiliary tools may include, for example, image capture probes, biopsy devices, laser ablation fibers, or other surgical, diagnostic, or therapeutic tools. Auxiliary tools may include end effectors having a single working member such as a scalpel, a blade, an optical fiber, or an electrode. Other end effectors may include a pair or plurality of working members such as forceps, graspers, scissors, or clip appliers, for example. Examples of electrically activated end effectors include electrosurgical electrodes, transducers, sensors, and the like. In various embodiments, the auxiliary tool 226 may be an image capture probe including a distal portion with a stereoscopic or monoscopic camera disposed near the distal end 218 of the flexible catheter body 216 for capturing images (including video images) that are processed for display. The image capture probe may include a cable coupled to the camera for transmitting the captured image data. Alternatively, the image capture instrument may be a fiber-optic bundle, such as a fiberscope, that couples to the imaging system. The image capture instrument may be single or multi-spectral, for example capturing image data in the visible spectrum, or capturing image data in the visible and infrared or ultraviolet spectrums.

The flexible catheter body 216 may also house cables, linkages, or other steering controls (not shown) that extend between the instrument body 204 and the distal end 218 to controllably bend or turn the distal end 218 as shown for example by the dotted line versions of the distal end. In embodiments in which the instrument system 200 is actuated by a robotic assembly, the instrument body 204 may include drive inputs that couple to motorized drive elements of the robotic assembly. In embodiments in which the instrument system 200 is manually operated, the instrument body 204 may include gripping features, manual actuators, and other components for manually controlling the motion of the instrument system. The catheter system may be steerable or, alternatively, may be non-steerable with no integrated mechanism for operator control of the instrument bending. Also or alternatively, the flexible body 216 can define one or more lumens through which interventional instruments can be deployed and used at a target surgical location.

In various embodiments, the interventional instrument system 200 may include a flexible bronchial instrument, such as a bronchoscope or bronchial catheter for use in examination, diagnosis, biopsy, or treatment of a lung. The system is also suited for navigation and treatment of other tissues, via natural or surgically created connected passageways, in any of a variety of anatomical systems including the colon, the intestines, the kidneys, the brain, the heart, the circulatory system, or the like.

When operating an interventional instrument system 200 within a patient it may be desirable for the surgeon to have simultaneous access to various forms of data related to the operation, as described herein. For instance, when guiding an interventional instrument through certain portions of the anatomy such as the respiratory system, an endoscope may be too large to fit safely through the anatomy alongside the interventional instrument system 200. In such operations the surgeon may wish to supplement the display of an endoscopic camera with the display of preoperative images of the type described above. Additionally, the surgeon may wish to supplement the display of an endoscopic camera with the display of a stylized representation of the location of the interventional instrument relative to the operation site or a particular target location within the anatomy.

Figure 3:
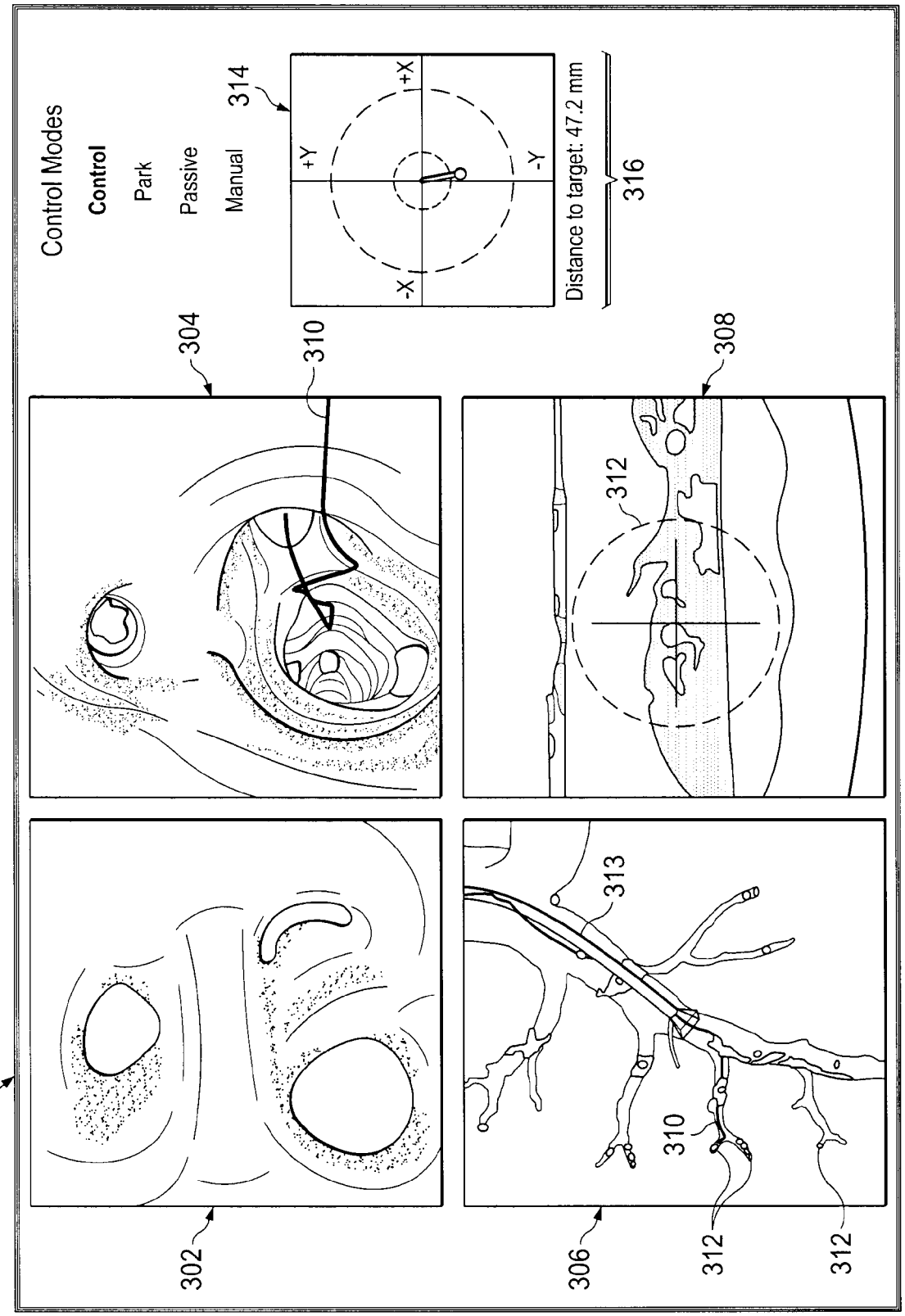
FIG. 3 illustrates a graphical user interface for displaying information related to the positioning guidance of an interventional instrument system.

FIG. 3 illustrates a two dimensional graphical user interface (GUI) 300 displayable on display system 110. The GUI 300 contains multiple windows which are simultaneously viewable to the surgeon via the display system 110. These windows may display such things as images representative of the patient's anatomy, images representative of the location of an interventional instrument, guidance information for the surgeon, and other information relevant to the operation. In the embodiment of FIG. 3, the GUI contains an endoscopic camera image 302 generated by an endoscopic camera within the patient anatomy, a virtual endoscopic image 304 generated from pre-operative or intra-operative imaging processed by the virtual visualization system, a virtual overview pathway image 306 providing an overview of the anatomical passageway system and generated from pre-operative or intra-operative imaging processed by the virtual visualization system, a multi-planar reconstruction image 308 showing a cross section of a set of pre-operative or intra-operative images at the location of a registered pose, and a navigation aid image 314.

In this embodiment, the GUI 300 additionally contains guidance information in the form of a virtual roadmap 310 which may be overlaid onto images in the GUI as demonstrated in images 304 and 306. The virtual roadmap 310 may be used by the surgeon to guide insertion of the interventional instrument 200 in order to reach target locations 312 which are identified before or during surgery. Such target locations 312 may also be incorporated into (e.g., overlaid, superimposed, otherwise combined with) any of the images in the GUI as demonstrated in images 306 and 308. A target location may include, for example, a tumor which the surgeon intends to remove or biopsy, a part of the anatomy which the surgeon intends to image or analyze with equipment in the interventional instrument system 200, a bifurcation in an anatomical passageway, a lumen of an anatomical passageway, or a waypoint location on the virtual roadmap which will allow the surgeon to navigate the interventional instrument towards an ultimate target location via an indirect route through the patient's anatomy. One or more of the constituent images of the GUI 300 may include a virtual image of the interventional instrument 313 superimposed on or otherwise incorporated into a virtual or endoscopic image. The GUI may also include other information relevant to the surgery, such as a distance display 316 showing the distance remaining from the distal end 218 (also referred to as the tip portion) of the interventional instrument 200 to a target location 312. In this embodiment, the displayed distance 316 may be calculated as the Euclidean distance between the tip portion and the target location.

The GUI 300 may also provide triggered guidance information to the surgeon based on the position of the tip portion of the interventional instrument. For example if the tip portion has passed an anatomical target, a provided alert will instruct the surgeon to retract the catheter, thus preventing the surgeon from further misrouting the interventional instrument or injuring the patient by directing the interventional instrument into healthy tissue. In some embodiments this triggered guidance information may be displayed in one of the windows of the GUI 300. For example, a visual cue (e.g. a flashing icon, change in color, or an alphanumeric message) may be displayed on the virtual overview pathway image 306 alerting the surgeon that an anatomical target or turning point has been bypassed. Alternatively, the triggered guidance may be visually provided elsewhere on the GUI 300 including, for example, a flashing icon on the display or a flashing block of color suffusing the background of the display. In still other embodiments, the triggered feedback may take the form of an audible alert including, for example, an alarm or playing of a vocal recording. In yet other embodiments, the triggered feedback may take the form of haptic feedback including, for example, a vibration in the control devices of input system 106. In some embodiments the feedback might be triggered when the tip portion is nearing a target location, when the tip portion has passed a target location, when the tip portion is moving directly toward a target location, or when the tip portion is moving away from a target location. A single embodiment may include multiple different types of feedback triggered based on different conditions.

Figure 4:
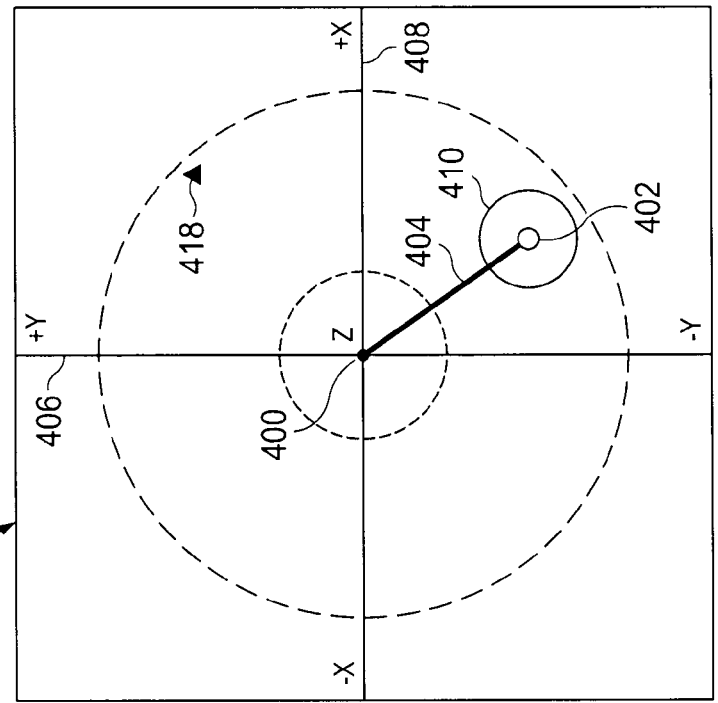
FIG. 4 illustrates a navigation aid view of the graphical user interface according to one embodiment of the present disclosure.

Referring now to FIG. 4, there is illustrated a detailed view of an embodiment of the navigation aid image 314. The navigation aid image 314 provides an adaptive targeting system that provides information about distance and direction for use by a surgeon when guiding the tip portion 218 of an interventional instrument to a target location. The image 314 is updated as the tip portion 218 is moved within the patient anatomy to provide the surgeon with current information about the position and orientation of the tip portion relative to the target location. This image provides the surgeon with directional and positional information to guide the tip portion 218 of the interventional instrument to a target location 312. A symbol 400 representing the location of the tip portion 218 of the interventional instrument is located in the center of image 314. In this embodiment, the symbol 400 is the center of a set of cross-hairs, but in alternative embodiments, other icons or shapes may be used to represent the location of the tip portion 218 of the interventional instrument. Line 406 of the cross hairs is aligned with an up/down, or Y axis, translational degree of freedom while line 408 of the cross hairs is aligned with a right/left, or X axis, translational degree of freedom of the tip portion 218 of the interventional instrument. Symbol 402 represents the target location 312. In this embodiment, the symbol 402 is a circle, but other shapes or icons may be used in the alternative. Symbol 404 connects the tip portion symbol 400 and target location symbol 402 and provides an indication of the direction the tip portion needs to be guided in order to move towards the target location 312. In this embodiment, the symbol 404 is a line, but in alternative embodiments the direction indicator symbol may be an arrow or another type of icon. A third translational degree of freedom, insertion/extraction or distance along a Z-axis (into or out of the plane of the two-dimensional image 314), of the tip portion 218 of the interventional instrument is indicated by symbol 410. In this embodiment, the symbol 410 is a circle concentric with target location symbol 402, but in alternative embodiments, other icons or shapes may be used to indicate the insertion distance between the tip portion 218 of the interventional instrument and the target location.

Optionally, the navigation aid image 314 may display the distance between the tip portion 218 and the target location 312 numerically, with an X-dimension distance component, a Y-dimension distance component, and/or a Z-dimension distance component. The distance equation used is:

$$\text{Distance to Target} = \sqrt{(x2-x1)^2 + (y2-y1)^2 + (z2-z1)^2}$$

where (x2, y2, z2) is the location of the target and x1, y1, z1) is the position of the tip portion.

As the surgeon actuates the tip portion 218 of the interventional instrument in the X and Y dimensions, the position of the target location symbol 402 relative to the tip portion symbol 400 and will change accordingly within the navigation aid image 314. In this embodiment, the tip portion symbol 400 is the frame of reference for image 314 so the target location symbol 402 will move to represent the tip portion's new location relative to the actual target location 312. The direction indication symbol 404 may pivot about the tip portion symbol 400 to indicate to the surgeon the X-Y direction to steer the tip portion 218 of the catheter directly towards the target location 312. In some embodiments, the direction indication symbol 404 may also scale in length as the tip portion moves to represent the remaining distance in the X and Y dimensions that the tip portion must be moved in order to be pointing directly towards target location 312.

As the surgeon actuates the tip portion 218 of the interventional instrument in the Z dimension, the distance display 316 will display the changing distance between the tip portion and the target location 312. Additionally, the insertion dimension symbol 410 may scale in size, for example getting smaller as the distance between the tip portion 218 and the target location 312 decreases and larger as the distance increases. In various embodiments, one or both of the distance indicators 316, 410 may be optional. In various other embodiments, a three dimensional display may be provided, allowing the surgeon to view the scaled distance between the tip portion and target location in the Z-dimension of the three-dimensional display.

Figure 5:
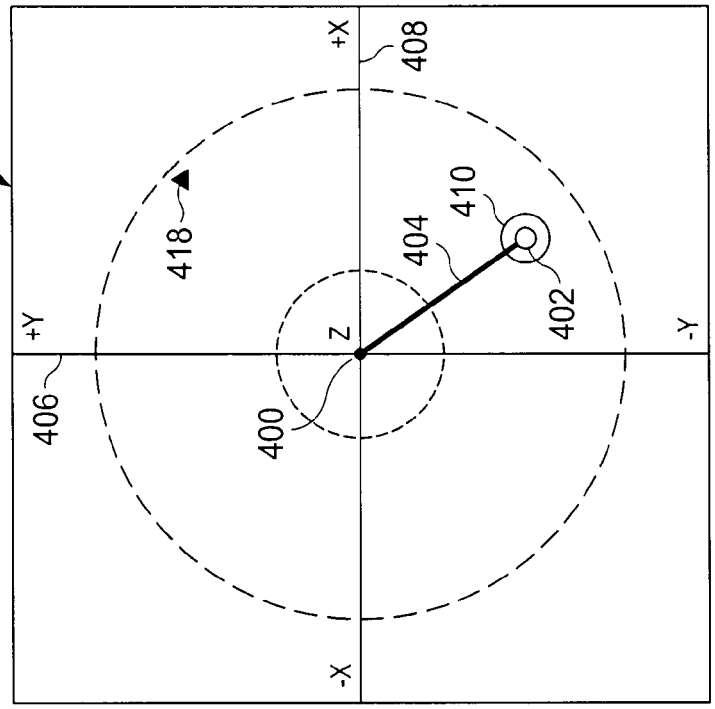
FIG. 5 illustrates the navigation aid view of FIG. 4 in a different state of information display.

FIG. 5 illustrates a change in the position of the tip portion 218 relative to the target location 312 as compared to FIG. 4. In this view of the navigation aid image 314, the Z distance between the tip portion 218 and the target location 312 has been reduced. The Z dimension symbol 410 is reduced to almost the same size as the target location symbol 402 to indicate that the tip portion 218 is close to the target location 312 along the Z-dimension. However, the tip portion must still be guided in the X and Y dimensions as indicated by direction indication symbol 404 to reach the target location 312.

As the surgeon guides the tip portion 218 of the interventional instrument through the patient's anatomy he may also actuate the tip portion in a rotational degree of freedom, i.e, rotationally about the Z-axis. If the distal tip portion 218 of the instrument is not circular or has a preferred rotational angle of deployment, the rotational orientation of a feature of the distal tip portion 218 may also be displayed by the navigation aid image with a rotation assistance symbol 418. For example, if a biopsy instrument has a side opening, the side with the opening may be indicated on the navigation aid image with the rotation assistance symbol 418.

Figure 6:
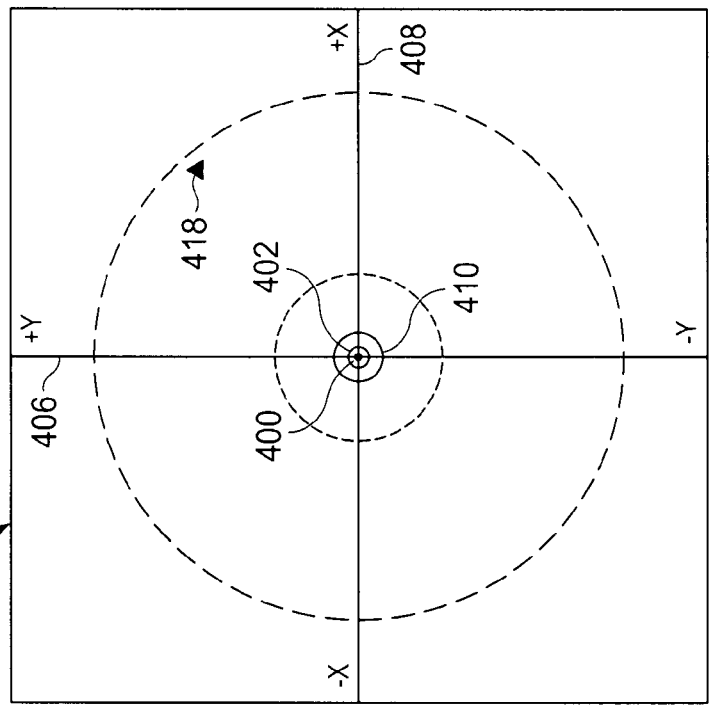
FIG. 6 illustrates the navigation aid view of FIG. 4 in yet another state of information display.

FIG. 6 illustrates a change in position of the tip portion 218 relative to the target location 312 as compared to FIGS. 4 and 5. In this view of the navigation aid image 314, the tip portion 218 of the interventional instrument has reached the target location 312. The tip portion is directly aligned in the X and Y dimensions with the target location 312 as represented by the target location symbol 402 being centered over the tip portion symbol 400, in addition to the Z dimension symbol 410 being minimized as was shown in FIG. 5. If the target location 312 was the ultimate target (rather than a waypoint or other intermediate point), such as a tumor or other operation site, then system may display an indication to that effect (e.g. a change in color or symbol) and the surgeon may perform the procedure. If the target location 312 was a waypoint along virtual roadmap 310 then the system may update target location 312 to the next waypoint and navigation aid image 314 and distance display 316 will accordingly be updated to help the surgeon to guide the tip portion 218 of the interventional instrument to the next target location.

Figure 7:
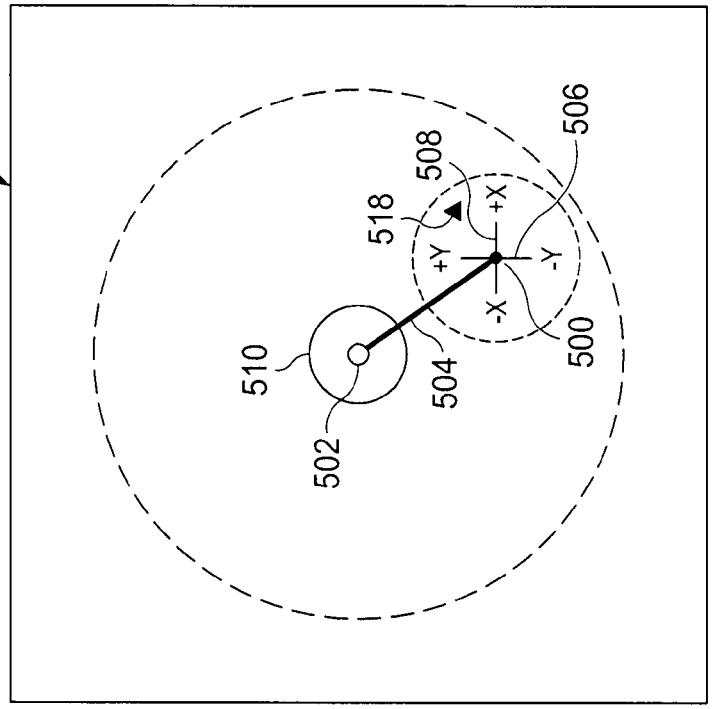
FIG. 7 illustrates a navigation aid view of the graphical user interface according to another embodiment of the present disclosure.

FIG. 7 illustrates an alternative embodiment of navigation aid image 314. In this embodiment, a target location symbol 502 is the frame of reference and is thus locked to the center of the image 314. In this embodiment, the target location symbol 502 is a circle, but in alternative embodiments may be a different type of shape or symbol. A Z-dimension symbol 510 is concentric with target location symbol 502. The Z-dimension symbol functions similar to the Z-dimension symbol 410 in FIG. 4 to indicate the Z-dimension distance between the instrument tip portion 218 and the target location 312. A tip portion symbol 500 is represented as the center of cross hairs with lines 506 and 508 aligned respectively with the Y and X translational degrees of freedom of the tip portion. When the surgeon actuates the tip portion 218 of the interventional instrument, the tip portion symbol 500 will move relative to target location symbol 502 to indicate the X and Y dimension change of the tip portion relative to the target location 312. Additionally X and Y degree of freedom symbols 506 and 508 will move such that they remain centered at tip portion symbol 500. This allows the surgeon to keep track of which dimension the tip portion must be actuated to move closer to target location 312.

Figure 8:
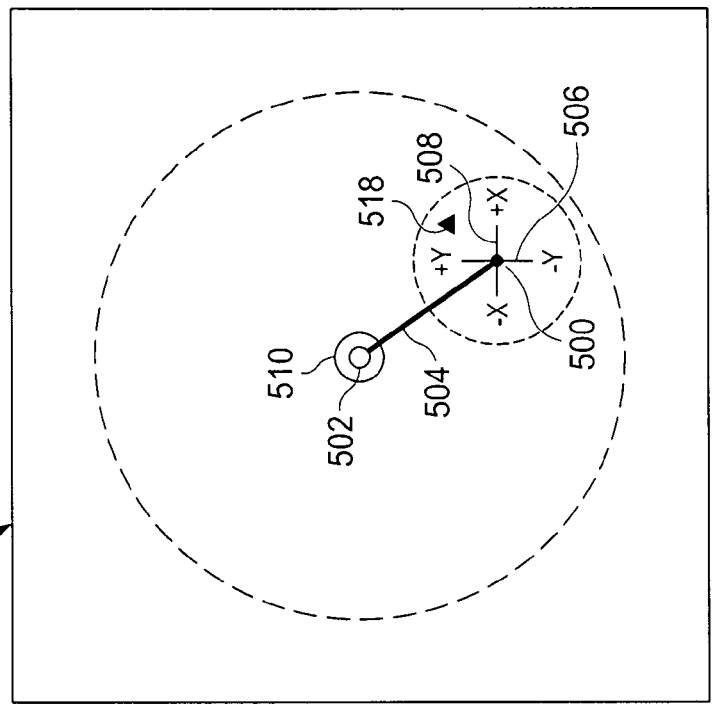
FIG. 8 illustrates the navigation aid view of FIG. 7 in a different state of information display.

FIG. 8 illustrates a change in the position of the tip portion 218 relative to the target location 312 as compared to FIG. 7. In this view of the navigation aid image 314, the Z distance is minimized, as represented by the smaller size of insertion dimension symbol 510. However, the tip portion is still not aligned in the X and Y dimensions with the target location 312. Direction indication symbol 504 shows where the surgeon needs to guide the tip portion to reach the target location 312.

Figure 9:
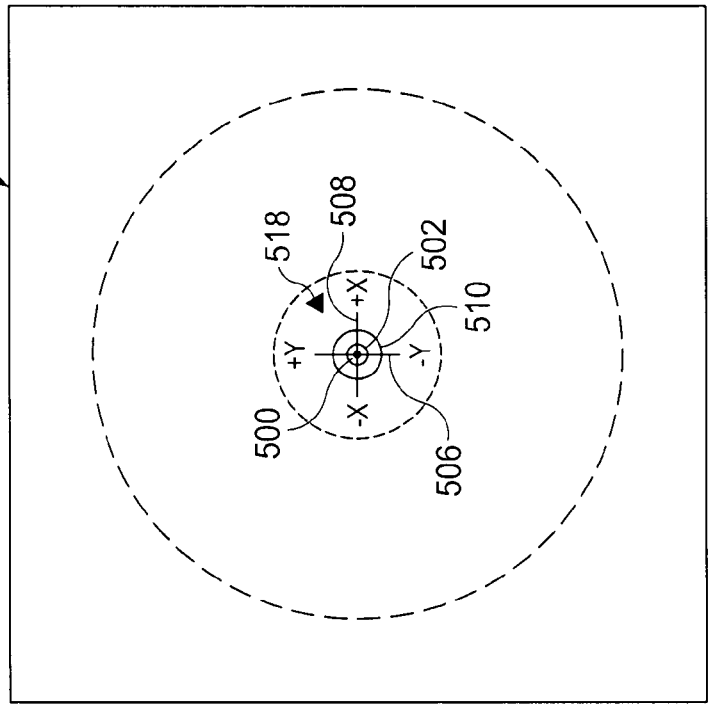
FIG. 9 illustrates the navigation aid view of FIG. 7 in yet another state of information display.

FIG. 9 illustrates a change in position of the tip portion 218 relative to the target location 312 as compared to FIGS. 7 and 8. In this view of the navigation aid image 314, the tip portion 218 of the interventional instrument has reached the target location 312, as indicated by the tip portion symbol 506 centered on target location symbol 502 and the small size of insertion dimension symbol 510 as was shown in in FIG. 5. The system may allow the surgeon to choose an embodiment of navigation aid image 314 dynamically to fit the surgeon's preference.

As the surgeon guides the tip portion of the interventional instrument through the patient's anatomy he may also actuate the tip portion in a rotational degree of freedom, i.e, rotationally about the Z-axis. If the distal tip portion 218 of the instrument is not circular or has a preferred rotational angle of deployment, the rotational orientation of a feature of the distal tip portion 218 may also be displayed by the navigation aid image with a rotation assistance symbol 518. For example, if a biopsy instrument has a side opening, the side with the opening may be indicated on the navigation aid image with the rotation assistance symbol 518.

In various embodiments, the images displayed in the composite windows of the GUI 300 are rotationally aligned. For example, if in FIG. 4 the target location symbol 402 is in the +X, −Y quadrant relative to the tip portion symbol 400, the image or icon associated with the target in the endoscopic image 302 and/or virtual visualization image 304 would be located in the lower right portion of the images. Additionally, the other images in the GUI 300, such as the virtual overview pathway image 306 and the pre-operative image 312 rotate appropriately to reflect the orientation of the tip portion. This will allow the surgeon to consistently perceive the orientation and alignment of the interventional instrument within the patient anatomy from multiple navigation assistance images.

Figure 10:
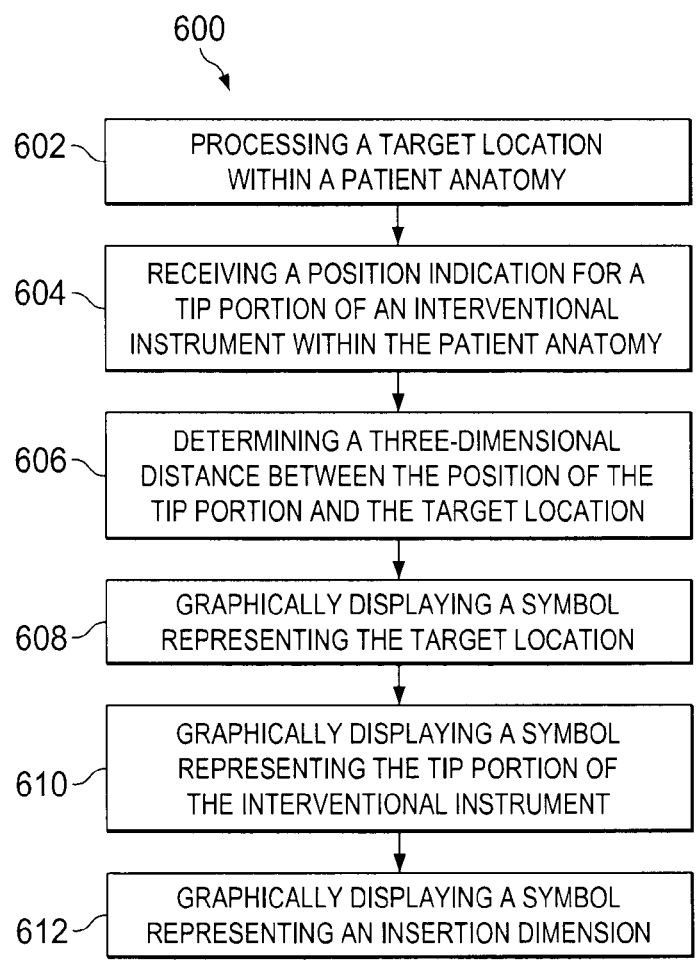
FIG. 10 is a flowchart describing a method of displaying information related to the positioning guidance of an interventional instrument system using a graphical user interface according to an embodiment of the present disclosure.

FIG. 10 illustrates a flow chart describing a method 600 of using the GUI 300 to aid in guiding the tip portion of an interventional instrument to a target location in a patient anatomy. At 602, the method 600 includes processing a target location within a patient anatomy. This may include, for example, selecting or identifying a target location or receiving a target location predetermined by another process. As described above, the target location may be a biopsy site, an operation site, a waypoint along a virtual roadmap ending at a procedure site, or the like. At 604, the method 600 includes receiving a position indication for a tip portion of an interventional instrument within the patient anatomy. At 606, the method 600 includes determining a three-dimensional distance between the position of the tip portion and the target location. At 608, the method 600 includes graphically displaying on the navigation aid image 314 a symbol representing the target location (e.g., the target location symbol 402 or 502). At 610, the method 600 includes graphically displaying a symbol representing the tip portion of the interventional instrument (e.g., the tip portion symbol 400 or 500). At 612, the method 600 includes graphically displaying on the navigation aid image 314 a symbol representing an insertion dimension (e.g., the Z-dimension symbol 410 or 510). As the surgeon viewing the navigation aid image 314 guides the tip portion of the interventional instrument toward the target location, the image 314 is updated to provide current navigation assistance. When the tip portion reaches the target, a visual cue (e.g., color change on the navigation aid, icon change on the navigation aid) alerts the surgeon that the target has been reached. The target location for tip portion of the instrument may, in some procedures, be spaced apart from the tissue to be accessed. For example, in a biopsy procedure, the target location for the tip portion may have sufficient spacing from the biopsy tissue to allow the extension of a needle from the catheter sheathing the needle.

One or more elements in embodiments of the invention may be implemented in software to execute on a processor of a computer system such as control system 112. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A method of guiding an interventional instrument within a patient anatomy, the method comprising:
   identifying a target location within the patient anatomy;
   receiving a position for a tip portion of an interventional instrument at a first location within the patient anatomy;
   determining a three-dimensional distance between the first location and the target location; and
   displaying on a display system an image that includes a symbol representing the target location, a symbol representing the tip portion of the interventional instrument, and a rotational assist symbol indicating a rotational orientation of a deployment feature of the tip portion, wherein as the tip portion of the interventional instrument is actuated, the image is displayed so that the symbol representing the tip portion of the interventional instrument is a frame of reference for the image and the symbol representing the target location moves with respect to the symbol representing the tip portion of the interventional instrument to represent a new location of the tip portion relative to the target location.

2. The method of claim 1 further comprising displaying a symbol representing a direction between the position of the tip portion and the target location.

3. The method of claim 1 further comprising displaying a symbol representing an insertion distance component of the three dimensional distance in addition to the symbol representing the target location, wherein the symbol representing the insertion distance component is displayed surrounding the symbol representing the target location, and wherein a size of the symbol representing the insertion distance scales as an insertion distance between the tip portion and the target location changes.

4. The method of claim 3 wherein the symbol representing the insertion distance component is concentric with the symbol representing the target location.

5. The method of claim 1 further comprising:
displaying the symbols representing the target location and tip portion in a first window of a display; and
displaying a symbol representing a direction between the target location and the tip portion in a second window of the display.

6. The method of claim 5 wherein the symbols in the first window are rotationally aligned with the symbol in the second window.

7. The method of claim 5 wherein the symbol representing the direction between the target location and the tip portion includes directional guidance information for directing the tip portion toward the target location.

8. The method of claim 1 further comprising:
displaying the symbols representing the target location and the tip portion in a first window of a display; and
displaying a secondary guidance image in a second window of the display.

9. The method of claim 8 further comprising, based on a position of the tip portion of the interventional instrument, providing an alert that the position of the tip portion should be adjusted, wherein displaying the secondary guidance image in the second window includes displaying the alert.

10. The method of claim 8 wherein displaying the secondary guidance image in the second window includes rotating the secondary guidance image to reflect an orientation of the tip portion.

11. A system comprising:
non-transitory computer readable media containing computer executable instructions for guiding an interventional instrument within a patient anatomy including:
instructions for identifying a target location within the patient anatomy;
instructions for receiving a position of a tip portion of an interventional instrument at a first location within the patient anatomy;
instructions for determining a three-dimensional distance between the first location and the target location; and
instructions for displaying on a display system an image that includes a symbol representing the target location, a symbol representing the tip portion of the interventional instrument, and a rotational assist symbol indicating a rotational orientation of a deployment feature of the tip portion,
wherein as the tip portion of the interventional instrument is actuated, the image is displayed so that the symbol representing the tip portion of the interventional instrument is a frame of reference for the image and the symbol representing the target location moves with respect to the symbol representing the tip portion of the interventional instrument to represent a new location of the tip portion relative to the target location.

12. The system of claim 11 further comprising instructions for displaying a symbol representing a direction between the position of the tip portion and the target location.

13. The system of claim 11 further comprising instructions for displaying a symbol representing an insertion distance component of the three dimensional distance in addition to the symbol representing the target location, wherein the symbol representing the insertion distance component is displayed surrounding the symbol representing the target location, and wherein a size of the symbol representing the insertion distance scales as an insertion distance between the tip portion and the target location changes.

14. The system of claim 13 wherein the symbol representing the insertion distance component is concentric with the symbol representing the target location.

15. The system of claim 11 further comprising:
instructions for displaying the symbols representing the target location and tip portion in a first window of a display; and
instructions for displaying a symbol representing a direction between the target location and the tip portion in a second window of the display.

16. The system of claim 15 wherein the symbols in the first window are rotationally aligned with the symbol in the second window.

17. The system of claim 15 wherein the symbol representing the direction between the target location and the tip portion includes directional guidance information for directing the tip portion toward the target location.

18. The system of claim 11 further comprising:
instructions for displaying the symbols representing the target location and tip portion in a first window of a display; and
instructions for displaying a secondary guidance image in a second window of the display.

19. The system of claim 18 further comprising, based on a position of the tip portion of the interventional instrument, instructions for providing an alert that the position of the tip portion should be adjusted, wherein displaying the secondary guidance image in the second window includes displaying the alert.

20. The system of claim 18 wherein displaying the secondary guidance image in the second window includes rotating the secondary guidance image to reflect an orientation of the tip portion.

* * * * *